United States Patent [19]

Sakurai et al.

[11] 4,429,171
[45] Jan. 31, 1984

[54] METHOD FOR MANUFACTURE OF ORTHOMETHYLATED PHENOL COMPOUNDS

[75] Inventors: Tokio Sakurai, Yokohama; Kyosuke Komiya, Kawasaki; Yoshihiko Mori, Kawasaki; Yoshiharu Kitahama, Kawasaki; Isamu Iwami, Zushi, all of Japan

[73] Assignee: Asahi-Dow Limited, Tokyo, Japan

[21] Appl. No.: 320,003

[22] Filed: Nov. 10, 1981

[30] Foreign Application Priority Data

Nov. 28, 1980 [JP] Japan ................................. 55-166725
Dec. 1, 1980 [JP] Japan ................................. 55-167964
Jan. 23, 1981 [JP] Japan ................................. 56-8112

[51] Int. Cl.$^3$ ............................................. C07C 37/16
[52] U.S. Cl. ................................ 568/804; 568/794
[58] Field of Search ................ 568/804, 794, 790, 789

[56] References Cited

U.S. PATENT DOCUMENTS

| 3,446,856 | 5/1969 | Hamilton, Jr. | 568/804 |
| 3,823,907 | 12/1975 | Kotanigawa et al. | 568/804 |
| 3,953,529 | 4/1976 | Yonemitsu et al. | 568/804 |
| 4,024,195 | 5/1977 | Yonemitsu et al. | 568/804 |
| 4,386,226 | 5/1983 | Adey et al. | 568/804 |

FOREIGN PATENT DOCUMENTS

| 47-37944 | 9/1972 | Japan | 568/804 |
| 51-12610 | 4/1976 | Japan | 568/804 |
| 717588 | 10/1954 | United Kingdom | 568/804 |
| 1212579 | 12/1970 | United Kingdom | 568/794 |

Primary Examiner—Werren B. Lone
Attorney, Agent, or Firm—Armstrong, Nikaido, Marmelstein & Kubovcik

[57] ABSTRACT

Manufacture of orthomethylated phenol compounds by the reaction of phenol compounds having a hydrogen atom at the ortho position and methanol is accomplished advantageously by a method which effects the reaction by use of a catalyst comprising (A) iron oxide, (B) indium oxide, and (C) at least one member selected from the group consisting of chromium oxide and silicon oxide. According to this method, the reaction permits the orthomethylated phenol compound to be produced in high yields for a long time because of the catalyst's excellent activity-retaining property. Since the ortho-position selectivity and the utilization ratio of methanol are high and, consequently, the utilization efficiency of raw materials is high, the method of this invention produces the orthomethylated phenol compound with high efficiency from the phenol compounds.

20 Claims, No Drawings

METHOD FOR MANUFACTURE OF ORTHOMETHYLATED PHENOL COMPOUNDS

BACKGROUND OF THE INVENTION

This invention relates to a method for the manufacture or orthomethylated phenol compounds by the methylation of phenols having at least one ortho-hydrogen.

The orthomethylated phenol compounds which are produced by the method of this invention are useful as industrial raw materials. For example, 2,6-xylenol is a raw material for polyphenylene oxide and ortho-cresol is a raw material for agricultural pesticides and pharmaceutical products.

Methods which produce orthomethylated phenol compounds by the vapor-phase catalytic reaction of a phenol compounds with methanol and consequently methylating the orthoposition of phenol compounds have already been known to the art. A number of catalysts have been proposed for use in this reaction.

For example, the method of British Pat. No. 717,588 methylates ortho-cresol using metal oxide, particularly aluminum oxide, as a catalyst. Since the activity and the selectivity for the ortho-position are low, this method produces the orthomethylated compound (2,6-xylenol) in low yields. Moreover, the method produces by-products such as meta-methylated and para-methylated phenols.

Since it is extremely difficult to isolate 2,6-xylenol from the reaction mixture containing such by-products, this method is neither technically nor economically advantageous.

The method of U.S. Pat. No. 3,446,856 carries out the reaction using magnesium oxide as a catalyst at a very high temperature of 475° to 600° C. Thus, it has a disadvantage that the energy consumption is large and the catalytic activity-retaining property is poor.

Among the catalysts which have low reaction temperatures and, therefore, prove advantageous from the standpoint of energy consumption, those containing iron oxide have found recognition.

For example, Japanese Patent Publication No. 12610/1976 produces 2,6-xylenol by effecting the reaction at 350° C. in the presence of a catalyst prepared from iron oxide and chromium oxide. This method, however, produces 2,6-xylenol in low yields.

Japanese Patent Publication No. 37944/1972 produces 2,6-xylenol by use of a catalyst composed of iron oxide and indium oxide in respective proportions such that the atomic ratio of indium to iron falls in the range of 9/1 to 1/9. Still, this method produces 2,6-xylenol in low yields and has a disadvantage that the proportion of the converted methanol which has been utilized effectively in the reaction with phenol and ortho-cresol to the whole converted methanol, namely the utilization ratio of methanol, is extremely low and the greater part of the converted methanol has just survived in a decomposed form.

The method of Japanese Patent Publication No. 1269/1977 (corresponding to U.S. Pat. No. 3,953,529, West German Pat. No. 2,428,056, and British Pat. No. 1,428,057) uses a catalyst composed of iron oxide, chromium oxide, and silicon oxide and that of Japanese Patent Publication No. 12692/1977 (corresponding to U.S. Pat. No. 4,024,195, West German Pat. No. 2,547,309, and British Pat. No. 1,507,478) uses a catalyst composed of iron oxide, chromium oxide, silicon oxide, and alkali metal compound respectively in the production of 2,6-xylenol. The inventors of this invention have reproduced these two catalysts by carefully following the disclosures and made studies thereon, to learn that although they are improved in activity and activity-retaining property over the other catalysts described above, they fall short of functioning satisfactorily.

The inventors, therefore, have continued extensive studies in search of a catalyst which exhibits high activity at a low reaction temperature enough for economy of energy consumption, excels in activity-retaining property, shows high ortho-position selectivity, and warrants high utilization ratio of methanol.

They have consequently found that the catalyst composed of iron oxide and indium oxide has, outside the range of percentage composition heretofore known to the art, a range of percentage composition (involving a smaller proportion of indium) in which the catalyst acquires higher activity, exhibits excellent ortho-position selectivity, and provides high utilization ratio of methanol.

A further study revealed, however, that the catalyst composed of iron oxide and indium oxide lost its catalytic activity rapidly. In other words, this catalyst has been confirmed to have a very poor activity-retaining property.

SUMMARY OF THE INVENTION

After a diligent study devoted to overcome this disadvantage, the inventors have now found that a catalyst composed of iron oxide and indium oxide and further incorporating at least one member selected from the group consisting of chromium oxide and silicon oxide acquires a notably improved activity-retaining property.

In addition, this catalyst shows improved activity and enables the orthomethylated phenol compound such as 2,6-xylenol to be produced in high yields.

Surprisingly, this remarkable effect is recognized over a wide range of the percentage composition of iron oxide and indium oxide.

The inventors' discovery has extended further. They have found that a catalyst which incorporates an alkali metal compounds besides iron oxide, indium oxide, and at least one member selected from the group consisting of chromium oxide and silicon oxide exhibits a yet better activity-retaining property.

The inventors' study based on the discovery has led to perfection of the method of the present invention.

This invention relates to a method for the manufacture of orthomethylated phenol compounds by the reaction of phenol compounds having at least one hydrogen atom at the ortho position thereof and methanol, characterized by effecting said reaction by use of a catalyst comprising:

A: iron oxide,
B: indium oxide, and
C: at least one member selected from the group consisting of chromium oxide and silicon oxide.

Further this invention relates to the method characterized by effecting said reaction by use of a catalyst comprising said components A, B, and C plus D: at least one alkali metal compound.

The catalyst of the present invention has very excellent activity and activity-retaining property. Such properties have been attained for the first time by incorporating chromium oxide, silicon oxide, and an alkali metal into iron oxide and indium oxide. These highly desirable properties would not have been attained by the prior art.

DETAILED DESCRIPTION OF THE INVENTION

The phenol compounds used as one raw material in this invention are required to have at least one hydrogen atom at the ortho position as represented by the general formula:

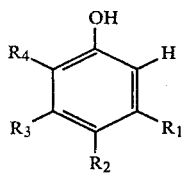

(wherein, $R_1$, $R_2$, $R_3$, and $R_4$ each denote a hydrogen atom or an alkyl group such as methyl or ethyl). Concrete examples of the phenol compounds fulfilling this requirement include phenol, ortho-cresol, meta-cresol, para-cresol, 2,3-xylenol, 2,4-xylenol, 3,4-xylenol, 3,5-xylenol, and other similar xylenols, orthoethyl phenol, ortho-isopropyl phenol, and ortho- or para-tert. butyl phenols.

This invention is effected by using either of the two catalysts described below:

(1) The catalyst comprising
A: iron oxide,
B: indium oxide, and
C: at least one member selected from the group consisting of chromium oxide and silicon oxide.

(2) The catalyst comprising the components A, B, and C described above plus at least one alkali metal compound.

Although these catalysts can be obtained in various percentage compositions, the atomic ratio of iron:indium:chromium:silicon:alkali metal is desired to fall in the range of 100:0.5~50:0 or 0.05~20:0 or 0.05~10:0 or 0.01~0.5, preferably in the range of 100:1~30:0 or 0.3~10:0 or 0.1~5:0 or 0.05~0.3, and most preferably in the range of 100:2~10:0 or 0.3~7.5:0 or 0.1~3:0 or 0.05~0.2, providing that chromium and silicon do not both assume 0 at the same time.

When the atomic ratio of indium to 100 atoms of iron is less than 0.5 or more than 50, the produced catalyst tends to acquire a slightly inferior activity and the yield of the orthomethylated phenol compound also tends to decrease slightly.

In the system containing chromium oxide alone as the component C, the activity-retaining property of the produced catalyst tends to decrease when the atomic ratio of chromium to 100 atoms of iron is less than 0.05. When the atomic ratio is more than 20, the produced catalyst tends to show a slightly inferior activity and require an undesirably high reaction temperature. In the system containing silicon oxide alone as the component C, similarly undesirable inclinations are observed when the atomic ratio of silicon to 100 atoms of iron deviates from the range of 0.05 to 10. In the system containing both chromium oxide and silicon oxide as the component C, the effect of using these two members as the component C, namely, the improvement of activity and activity-retaining property, clearly appears when the atomic ratio of chromium falls in the range of 0.05 to 20 and that of silicon in the range of 0.05 to 10 respectively relative to 100 atoms of iron.

In the system containing an alkali metal as the component D, the produced catalyst acquires higher activity and activity-retaining property than the catalyst containing no alkali metal. When the atomic ratio of the alkali metal to 100 atoms of iron is less than 0.01, the effect of the addition of the alkali metal in the improvement of activity-retaining property tends to lessen. When this atomic ratio exceeds 0.5, the produced catalyst tends to show an inferior activity.

In the composition of the catalyst of this invention, the iron oxide can be effectively used in any of the forms of various valences such as, for example, $Fe_2O_3$, $Fe_3O_4$, and $FeO$. Similarly, the indium oxide can be used in any of the forms of $In_2O_3$, $InO$, and $In_2O$ and the chromium oxide in any of the forms of $CrO$, $Cr_2O_3$, $CrO_2$, and $CrO_3$.

Examples of alkali metal compounds which are advantageously used in this invention include carbonates, hydroxides, nitrates, and sulfates of lithium, sodium, potassium, rubidium, and cesium. Among these compounds, carbonate, hydroxide, and nitrate of potassium prove particularly desirable.

The raw materials as the sources for iron oxide, indium oxide, and chromium oxide to be used in the preparation of the catalyst of this invention are hydroxides, chlorides and other halogenides, nitrates, sulfates, and organic acid salts of the respective metals. The raw materials as sources for silicon oxide include sodium silicate and other alkali silicates, silica sol, ethyl orthosilicate and other similar organic silicon compounds, and silicon tetrachloride.

The catalyst of this invention can be prepared by any of the various methods known in the art. For example, the preparation by the coprecipitation method involves the steps of neutralizing an aqueous solution containing an iron compound, an indium compound, and at least one member selected from among chromium compounds and silicon compounds with an alkali such as ammonia thereby coprecipitate the components of interest, washing the mixture, separating the coprecipitate by filtration, and drying and calcining the separated coprecipitate.

According to the blending method, the preparation is effected by the steps of thoroughly blending iron hydroxide, indium hydroxide, and either or both of chromium hydroxide and silica sol optionally in conjunction with a carrier or binder such as, for example, silicon carbide, diatomaceous earth, or alumina, and then drying and calcining the resultant mixture.

The preparation by the carrier method is accomplished by the steps of depositing an iron compound, an indium compound, and at least one member selected from among chromium compounds and silicon compounds on a granular carrier such as alumina, silicon carbide or diatomaceous earth and subsequently drying and calcining the resultant composite.

The catalyst additionally containing an alkali metal compound can be prepared by depositing or adsorbing the alkali metal compound on the dried product (yet to be calcined) prepared by the aforementioned method and subsequently dried and calcined.

The adsorption of the alkali metal compounds on the dried product can be effected by immersing the dried product in an aqueous solution of the alkali metal compound thereby allowing the alkali metal compound to be adsorbed and then separated by filtration. Alternatively, it may be effected by similarly immersing the dried product in an aqueous solution of the alkali metal compound and subsequently evaporating water by application of heat. Otherwise, it may be accomplished by spraying an aqueous solution of the alkali metal compound to the dried product and thereafter drying the wet product.

The calcining temperature involved in the preparation of the catalyst is generally in the range of 370° to 900° C., although it is more or less variable with the particular method of catalyst preparation.

The molar ratio of methanol to the phenol compounds to be used as the principal reactants in working out the present invention is desired to fall in the range of 1:1 to 10:1. When the ratio of methanol to one mole of phenol compounds is less than 1, the unaltered portion of the phenol compounds notably increases. When the ratio exceeds 10, by-products such as anisoles, paramethylated products, and gaseous products due to decomposition of methanol increase.

The principal reactants of the present invention can be diluted with an inert gas such as nitrogen or with methane, hydrogen, or water produced in the course of the reaction. Particularly, the dilution by use of water is desirable from the standpoint of enhancing the improvement of the catalyst's activity-retaining property. In this case, the suitable molar ratio of the phenol compounds to water is in the range of 1:0.1 to 1:10. When the molar ratio of water to one mole of phenol compounds is less than 0.1, the improvement aimed at falls short of the expected level. When this molar ratio is higher than 10, the concentration of the reactants is lowered and the productivity of the reaction is proportionally lowered.

The reaction temperature is in the range of 250° C. to 500° C., preferably 300° C. to 400° C. When the reaction temperature is less than 250° C., the reaction does not proceed thoroughly. When the reaction temperature exceeds 500° C., by-products such as anisoles, paramethylated products, and gaseous products due to decomposition of methanol increase.

The space velocity is desired to fall in the range of 0.05 to 10, preferably 0.1 to 5, by LHSV (cc/cat·cc·hr), although it is widely variable with the other reaction conditions. When the space velocity is less than 0.05, gaseous products due to decomposition of methanol increase. When it is more than 10, the reaction does not proceed thoroughly.

As regards the reaction pressure, the reaction can be effectively carried out under reduced pressure, under normal atmospheric pressure, or under increased pressure, whichever may be convenient for the particular occasion. The increased pressure desirably falls in the range of 0.5 to 50 kg/cm² G.

The reactor to be used herein may be in any of various forms of popular acceptance such as fixed bed, fluidized bed, and moving bed. When the reactor is in the form of fixed bed, the catalyst is desired to be used as diluted with alumina, silicon carbide, quartz sand, or crushed glass so as to preclude possible occurrence of local heat points.

The gas emanating from the reactor outlet is cooled, condensed or absorbed by an organic solvent and thereafter distilled to isolate the aimed product.

As described above, the method of this invention enables the orthomethylated phenol compounds to be produced in high yields for a long time. Further, since it shows high orthoposition selectivity and high utilization ratio of methanol, the reactants can be utilized efficiently. Thus, this method permits efficient production of an orthomethylated phenol compounds from a corresponding phenol compounds. It, thus, proves advantageous both from the technical and economical points of view.

Now, the present invention will be described specifically below with reference to working examples. The invention is not specifically limited by these working examples in any respect.

In the working examples, the results of reaction were rated by the factors defined below. The values involved are invariably based on mols.

Conversion of phenol compound as reactant =

$$\frac{\text{Phenol compound converted}}{\text{Phenol compound supplied}} \times 100$$

$$\text{Selectivity for 2,6-xylenol} = \frac{\text{2,6-xylenol produced}}{\text{Phenol compound converted}} \times 100$$

The selectivity for ortho-cresol, that for 2,4-xylenol, and that for 2,4,6-trimethyl phenol and the like were calculated in entirely the same way as that for 2,6-xylenol.

$$\text{Utilization ratio of methanol} = \frac{\text{Methanol reacted with phenol compound}}{\text{Methanol converted}} \times 100$$

EXAMPLE 1

In 400 cc of pure water, 20 gr. of ferric nitrate, Fe(NO$_3$)$_3$·9H$_2$O, 1.09 gr. of indium chloride, InCl$_4$·4H$_2$O, 0.2 gr. of chromium nitrate, Cr(NO$_3$)$_3$·9H$_2$O, and 0.11 gr. of aqueous sodium silicate solution (having a SiO$_2$ concentration of 30 weight percent) were dissolved. The resultant solution, while under agitation, was neutralized to pH 7.0 by gradual dropwise addition thereto of 10% ammonia water. The agitation of the solution was further continued for one hour at room temperature. Thereafter, the produced precipitate was washed with water, separated by filtration, and dried at 180° C. for five hours. A 10-gr. portion of the resultant particles 10 to 16 mesh was immersed in 12 ml of aqueous potassium carbonate solution (containing 0.2 gr. of K$_2$CO$_3$) at room temperature for 12 hours. Then, the particles were separated by filtration from the solution, dried at 150° C. for five hours, and calcined under a current of air at 470° C. for four hours to afford a catalyst of the iron oxide.indium oxide.chromium oxide.silicon oxide.-potassium carbonate system.

The composition of the produced catalyst as expressed by the atomic ratio of Fe:In:Cr:Si:K was 100:7.5:1:1:0.12.

Two (2) cc of the catalyst was placed in a reactor made of Pylex Glass measuring 18 mm in inside diameter and used for the following reaction.

A mixed solution of phenol, methanol, and water (molar ratio of phenol/methanol/water=1/5/5) was supplied at LHSV of 0.84 (cc/cat.cc.hr) to the reactant preheater zone of a reactor heated in advance to 250° C. to be vaporized therein. Then, the resultant vapor was passed through a catalyst bed kept at 350° C. to undergo a reaction.

The gas emanating from the reactor outlet was cooled by being passed through an air-cooled trap and deep-cooled trap (−78° C.). The liquid product recovered was analyzed by gas chromatography. The results are shown in Table 1.

EXAMPLE 2

In 400 cc of pure water, 20 gr. of ferric nitrate, 1.09 gr. of indium chloride, 0.2 gr. of chromium nitrate, and 0.11 gr. of aqueous sodium silicate solution (having a $SiO_2$ concentration of 30 weight percent) were dissolved. The resultant solution, while under agitation, was neutralized to pH 7.0 by gradual dropwise addition thereto of 10% ammonia water.

The agitation of the solution was further continued for one hour at room temperature. The produced precipitate was washed with water, separated by filtration, and then dried at 180° C. for five hours. The resultant particles 10 to 16 mesh were calcined at 470° C. for four hours under a current of air to afford a catalyst of the iron oxide.indium oxide.chromium oxide.silicon oxide system.

The composition of the produced catalyst as expressed by the atomic ratio of Fe:In:Cr:Si was 100:7.5:1:1.

The reaction of Example 1 was performed by following the procedure of Example 1, except that the catalyst produced herein was used. The results are as shown in Table 1.

TABLE 1

| No. | Example 1 | | | Example 2 | | |
|---|---|---|---|---|---|---|
| Catalyst (composition)* | Fe:In:Cr:Si:K (100:7.5:1:1:0.12) | | | Fe:In:Cr:Si (100:7.5:1:1) | | |
| Molar ratio | Phenol/methanol/water = 1/5/5 | | | Phenol/methanol/water = 1/5/5 | | |
| LHSV | 0.84 (cc/cat.cc · hr) | | | 0.84 (cc/cat.cc · hr) | | |
| Temperature | 350° C. | | | 350° C. | | |
| Reaction time (hour) | Conversion of phenol (%) | Selectivity (%) | | Conversion of phenol (%) | Selectivity (%) | |
| | | o-cresol | 2,6-xylenol | | o-cresol | 2,6-xylenol |
| 100 | 100 | 0.9 | 98.3 | 100 | 1.1 | 98.2 |
| 500 | 100 | 0.4 | 98.8 | 100 | 0.8 | 98.5 |
| 1000 | 100 | 0.3 | 98.9 | 99.5 | 2.1 | 97.0 |
| 1500 | 100 | 0.5 | 98.7 | 98.7 | 4.9 | 94.2 |
| 2000 | 99.4 | 1.1 | 98.0 | 97.9 | 5.8 | 92.4 |
| 2500 | 99.0 | 2.1 | 97.1 | 97.1 | 11.6 | 87.5 |
| 2750 | 98.8 | 2.9 | 96.4 | 96.4 | 16.2 | 83.0 |
| 3000 | 98.6 | 3.3 | 96.0 | 95.3 | 25.6 | 73.5 |
| 4000 | 98.1 | 5.3 | 94.0 | | | |
| 4500 | 97.7 | 6.0 | 93.4 | | | |
| 5000 | 97.3 | 6.9 | 92.5 | | | |

*atomic ratio

EXAMPLE 3

A reactant solution consisting of phenol, methanol, and water in a molar ratio of 1:5:1 was subjected to reaction by using a catalyst (of a composition having an atomic ratio, Fe:In:Cr:Si:K, of 100:7.5:1:1:0.2) prepared by the procedure of Example 1 and following the procedure of Example 1, except that the reactant solution was supplied at a rate of 0.68 cc/cat.cc.hr in LHSV. The results are as shown in Table 2.

COMPARATIVE EXPERIMENT 1

The reaction of Example 3 was repeated, except that an iron oxide.silicon oxide.chromium oxide.potassium carbonate catalyst (of a composition having an atomic ratio, Fe:Si:Cr:K, of 100:1:1:0.2) prepared by following the procedure of Example 1 was used. The results are as shown in Table 2.

TABLE 2

| No. | Example 3 | | | Comparative Experiment 1 | | |
|---|---|---|---|---|---|---|
| Catalyst (composition)* | Fe:In:Cr:Si:K (100:7.5:1:1:0.2) | | | Fe:Si:Cr:K (100:1:1:0.2) | | |
| Molar ratio | Phenol/methanol/water = 1/5/1 | | | Phenol/methanol/water = 1/5/1 | | |
| LHSV | 0.68 (cc/cat.cc · hr) | | | 0.68 (cc/cat.cc · hr) | | |
| Temperature | 350° C. | | | 350° C. | | |
| Reaction time (hour) | Conversion of phenol (%) | Selectivity (%) | | Conversion of phenol (%) | Selectivity (%) | |
| | | o-cresol | 2,6-xylenol | | o-cresol | 2,6-xylenol |
| 24 | 100 | 0.7 | 98.3 | 100 | 2.8 | 94.4 |
| 100 | 100 | 0.1 | 99.5 | 99.8 | 4.9 | 92.7 |
| 150 | 100 | 0.1 | 99.5 | 99.3 | 13.0 | 85.4 |
| 200 | 100 | 0 | 99.6 | 97.5 | 18.0 | 80.6 |
| 250 | 100 | 0.1 | 99.4 | 93.2 | 41.9 | 57.3 |
| 350 | 100 | 0.1 | 99.3 | | | |
| 500 | 99.8 | 0.6 | 98.8 | | | |
| 700 | 99.0 | 1.6 | 97.7 | | | |
| 850 | 98.3 | 4.1 | 95.2 | | | |
| 1000 | 97.0 | 6.9 | 92.5 | | | |

*atomic ratio

EXAMPLE 4

The reaction of Example 3 was repeated, except that an iron oxide.indium oxide.chromium oxide.silicon oxide catalyst (of a composition having an atomic ratio, Fe:In:Cr:Si, of 100:7.5:1:1) prepared by following the procedure of Example 2 was used. The results are as shown in Table 3.

COMPARATIVE EXPERIMENT 2

The reaction of Example 3 was repeated, except that an iron oxide.silicon oxide.chromium oxide catalyst (of a composition having an atomic ratio, Fe:Si:Cr, of 100:1:1) prepared by following the procedure of Example 2 was used. The results are as shown in Table 3.

TABLE 3

| No. | Example 4 | | | Comparative Experiment 2 | | |
|---|---|---|---|---|---|---|
| Catalyst (composition)* | Fe:In:Cr:Si (100:7.5:1:1) | | | Fe:Si:Cr (100:1:1) | | |
| Molar ratio | Phenol/methanol/water = 1/5/1 | | | Phenol/methanol/water = 1/5/1 | | |
| LHSV | 0.68 (cc/cat.cc · hr) | | | 0.68 (cc/cat.cc · hr) | | |
| Temperature | 350° C. | | | 350° C. | | |
| Reaction time (hour) | Conversion of phenol (%) | Selectivity (%) | | Conversion of phenol (%) | Selectivity (%) | |
| | | o-cresol | 2,6-xylenol | | o-cresol | 2,6-xylenol |
| 24 | 100 | 0.9 | 98.1 | 99.9 | 3.9 | 93.4 |
| 50 | 100 | 0.4 | 99.2 | 99.9 | 5.6 | 92.1 |
| 100 | 100 | 0.3 | 99.4 | 99.4 | 10.3 | 87.6 |
| 150 | 100 | 0.3 | 99.5 | 92.0 | 46.8 | 52.3 |
| 200 | 100 | 0.4 | 99.4 | | | |
| 250 | 100 | 0.7 | 99.0 | | | |
| 300 | 99.2 | 0.8 | 98.9 | | | |
| 400 | 98.5 | 3.5 | 96.0 | | | |
| 500 | 97.2 | 6.4 | 93.0 | | | |

*atomic ratio

EXAMPLES 5 AND 6

The reaction of Example 3 was repeated, except that an iron oxide.indium oxide.chromium oxide.potassium carbonate catalyst (of a composition having an atomic ratio, Fe:In:Cr:K, of 100:7.5:2:0.05) prepared by following the procedure of Example 1 and an iron oxide.indium oxide.chromium oxide catalyst (of a composition having an atomic ratio, Fe:In:Cr, of 100:7.5:2) prepared by following the procedure of Example 1 were used respectively. The results are as shown in Table 4.

TABLE 4

| No. | Example 5 | | | Example 6 | | |
|---|---|---|---|---|---|---|
| Catalyst (Composition)* | Fe:In:Cr:K (100:7.5:2:0.05) | | | Fe:In:Cr (100:7.5:2) | | |
| Molar ratio | Phenol/methanol/water = 1/5/1 | | | Phenol/methanol/water = 1/5/1 | | |
| LHSV | 0.68 (cc/cat.cc · hr) | | | 0.68 (cc/cat.cc · hr) | | |
| Temperature | 350° C. | | | 350° C. | | |
| Reaction time (hour) | Conversion of phenol (%) | Selectivity (%) | | Conversion of phenol (%) | Selectivity (%) | |
| | | o-cresol | 2,6-xylenol | | o-cresol | 2,6-xylenol |
| 24 | 100 | 2.4 | 96.6 | 99.8 | 1.9 | 96.4 |
| 50 | 100 | 1.2 | 98.0 | 100 | 1.0 | 97.4 |
| 100 | 100 | 0.8 | 98.6 | 100 | 0.5 | 98.1 |
| 200 | 100 | 0.7 | 98.6 | 100 | 1.3 | 97.4 |
| 300 | 100 | 0.8 | 98.4 | 100 | 6.2 | 92.5 |
| 400 | 99.9 | 4.7 | 94.5 | 98.0 | 13.7 | 85.2 |
| 500 | 99.3 | 8.7 | 90.5 | | | |
| 600 | 98.1 | 11.9 | 87.4 | | | |

*atomic ratio

EXAMPLES 7 AND 8

The reaction of Example 3 was repeated, except that an iron oxide.indium oxide.silicon oxide.potassium carbonate catalyst (of a composition having an atomic ratio, Fe:In:Si:K, of 100:7.5:1:0.16) prepared by following the procedure of Example 1 and an iron oxide.indium oxide.silicon oxide catalyst (of a composition having an atomic ratio, Fe:In:Si, of 100:7.5:1) prepared by following the procedure of Example 2 were respectively used. The results are as shown in Table 5.

TABLE 5

| No. | Example 7 | | | Example 8 | | |
|---|---|---|---|---|---|---|
| catalyst (composition)* | Fe:In:Si:K (100:7.5:1:0.16) | | | Fe:In:Si (100:7.5:1:1) | | |
| Molar ratio | Phenol/methanol/water = 1/5/1 | | | Phenol/methanol/water = 1/5/1 | | |
| LHSV | 0.68 (cc/cat.cc · hr) | | | 0.68 (cc/cat.cc · hr) | | |
| Temperature | 350° C. | | | 350° C. | | |
| Reaction time (hour) | Conversion of phenol (%) | Selectivity (%) | | Conversion of phenol (%) | Selectivity (%) | |
| | | o-cresol | 2,6-xylenol | | o-cresol | 2,6-xylenol |
| 50 | 100 | 1.2 | 98.4 | 99.9 | 0.6 | 98.3 |
| 100 | 100 | 1.0 | 98.3 | 99.9 | 5.3 | 93.1 |
| 150 | 99.9 | 2.1 | 97.0 | 99.0 | 13.6 | 85.0 |
| 200 | 99.8 | 4.1 | 95.2 | 96.5 | 25.9 | 73.2 |
| 250 | 99.8 | 4.4 | 94.8 | | | |
| 300 | 99.2 | 8.2 | 91.0 | | | |
| 350 | 98.2 | 12.0 | 87.3 | | | |
| 400 | 97.0 | 14.3 | 84.9 | | | |

*atomic ratio

EXAMPLE 9

A reactant solution consisting of phenol, methanol, and water in a molar ratio of 1:7:3 was supplied at a rate of 1.0 cc/cat.cc.hr in LHSV and subjected to reaction at 340° C.-350° C. in the presence of a varying iron oxide.indium oxide.chromium oxide.silicon oxide.potassium carbonate catalyst of different composition prepared by following the procedure of Example 1. The results of the reaction obtained at prescribed intervals of time are summarized in Table 6.

TABLE 6

| No. | Example 9 | | | | | |
|---|---|---|---|---|---|---|
| Catalyst (Composition)* | Fe:In:Cr:Si:K (100:10:2:1:0.1) | | | Fe:In:Cr:Si:K (100:2:1:0.5:0.16) | | |
| Molar ratio | Phenol/methanol/water = 1/7/3 | | | Phenol/methanol/water = 1/7/3 | | |
| LHSV | 1.0 (cc/cat.cc · hr) | | | 1.0 (cc/cat.cc · hr) | | |
| Temperature | 340-350° C. | | | 340-350° C. | | |
| Reaction time (hour) | Conversion of phenol (%) | Selectivity (%) | | Conversion of phenol (%) | Selectivity (%) | |
| | | o-cresol | 2,6-xylenol | | o-cresol | 2,6-xylenol |
| 500 | 99.9 | 0.4 | 98.6 | 98.9 | 6.3 | 92.6 |
| 1000 | 99.9 | 0.5 | 98.5 | 99.0 | 6.2 | 92.7 |
| 1500 | 99.9 | 0.6 | 98.5 | 98.9 | 6.3 | 92.6 |
| 2000 | 99.8 | 0.6 | 98.4 | 98.7 | 6.5 | 92.4 |
| 2500 | 98.9 | 4.1 | 95.0 | 97.9 | 7.0 | 91.8 |
| 2750 | 98.3 | 6.9 | 92.1 | 97.8 | 8.5 | 90.5 |
| 3000 | 97.6 | 9.6 | 89.5 | 97.3 | 13.7 | 85.4 |

*atomic ratio

EXAMPLE 10

A reactant solution consisting of phenol, methanol, and water at a molar ratio of 1:5:1 was supplied at a flow rate of 1.6 cc/cat.cc.hr in LHSV and subjected to reaction at 350° C. in the presence of a varying iron oxide.indium oxide.chromium oxide catalyst or iron oxide.indium oxide.silicon oxide catalyst of a different composition prepared by following the procedure of Example 2. The results of the reaction obtained at 8 hours' reaction time are summarized in Table 7.

TABLE 7

| | No. Example 10 | | | | |
|---|---|---|---|---|---|
| Catalyst Composition (by atomic ratio) | Conversion of phenol (%) | Selectivity (%) | | | |
| | | o-cresol | 2,6-xylenol | 2,4,6-trimethyl phenol | Others |
| Fe:In:Cr(100:2:0.3) | 85.6 | 20.7 | 78.7 | 0.5 | 0.1 |
| Fe:In:Cr(100:3.5:2) | 95.2 | 18.2 | 81.1 | 0.5 | 0.2 |
| Fe:In:Cr(100:5:2) | 94.0 | 14.4 | 85.0 | 0.4 | 0.2 |
| Fe:In:Cr(100:10:5) | 97.1 | 7.8 | 91.5 | 0.5 | 0.2 |
| Fe:In:Cr(100:20:5) | 97.2 | 9.2 | 90.0 | 0.5 | 0.3 |
| Fe:In:Cr(100:30:5) | 97.4 | 16.1 | 83.4 | 0.4 | 0.1 |
| Fe:In:Cr(100:50:10) | 85.3 | 44.9 | 54.2 | 0.6 | 0.3 |
| Fe:In:Cr(100:7.5:7.5) | 96.2 | 4.8 | 94.4 | 0.6 | 0.2 |
| Fe:In:Cr(100:3.5:0.05) | 82.4 | 29.6 | 70.6 | 0.6 | 0.2 |
| Fe:In:Cr(100:50:20) | 80.3 | 54.0 | 45.1 | 0.7 | 0.1 |
| Fe:In:Cr(100:30:15) | 93.1 | 20.7 | 78.3 | 0.6 | 0.2 |
| Fe:In:Si(100:1:2) | 81.8 | 59.2 | 40.1 | 0.6 | 0.1 |
| Fe:In:Si(100:1:0.1) | 83.1 | 35.0 | 64.3 | 0.6 | 0.2 |
| Fe:In:Si(100:2:1) | 85.0 | 33.7 | 65.4 | 0.7 | 0.2 |
| Fe:In:Si(100:3.5:1) | 98.2 | 7.6 | 91.8 | 0.5 | 0.1 |
| Fe:In:Si(100:5:2) | 94.1 | 16.6 | 83.0 | 0.3 | 0.1 |
| Fe:In:Si(100:7.5:0.05) | 91.6 | 26.9 | 72.3 | 0.6 | 0.2 |
| Fe:In:Si(100:10:2) | 98.0 | 6.0 | 93.3 | 0.5 | 0.2 |
| Fe:In:Si(100:20:0.5) | 97.5 | 7.1 | 92.0 | 0.7 | 0.2 |
| Fe:In:Si(100:30:2) | 99.3 | 7.0 | 92.0 | 0.7 | 0.3 |
| Fe:In:Si(100:30:5) | 96.8 | 8.6 | 90.4 | 0.7 | 0.3 |
| Fe:In:Si(100:50:7.5) | 92.4 | 13.7 | 85.4 | 0.6 | 0.3 |
| Fe:In:Si(100:50:10) | 91.5 | 27.3 | 71.8 | 0.7 | 0.2 |
| Fe:In:Si(100:30:15) | 82.0 | 60.4 | 38.8 | 0.6 | 0.2 |

EXAMPLE 11

A reactant solution consisting of phenol, methanol, and water in a molar ratio of 1:5:5 was supplied at a rate of 2.0 cc/cat.cc.hr. in LHSV and subjected to reaction at a temperature of 350° C. in the presence of a varying iron oxide.indium oxide.chromium oxide.silicon oxide catalyst of a different composition prepared by following the procedure of Example 2. The results of reaction obtained at 8 hours' reaction time are summarized in Table 8.

TABLE 8

| | | No. Example 11 | | | |
|---|---|---|---|---|---|
| Catalyst composition (Fe:In:Cr:Si by atomic ratio) | Conversion of phenol (%) | Selectivity (%) | | | |
| | | o-cresol | 2,6-xylenol | 2,4,6-trimethyl phenol | Others |
| 100:1:1:1 | 88.2 | 33.9 | 65.2 | 0.8 | 0.1 |
| 100:2:1:0.05 | 90.7 | 22.8 | 76.3 | 0.8 | 0.1 |
| 100:3.5:0.05:1 | 92.4 | 18.6 | 80.5 | 0.8 | 0.1 |
| 100:5:2:2 | 95.1 | 6.8 | 92.1 | 0.9 | 0.2 |
| 100:7.5:5:0.1 | 99.8 | 5.0 | 94.1 | 0.7 | 0.2 |
| 100:10:0.3:1 | 99.8 | 4.7 | 94.4 | 0.7 | 0.2 |
| 100:20:3.5:5 | 97.2 | 8.5 | 90.6 | 0.6 | 0.3 |
| 100:20:10:3 | 98.3 | 7.7 | 91.4 | 0.7 | 0.2 |
| 100:30:2:7.5 | 99.0 | 5.5 | 93.5 | 0.8 | 0.2 |
| 100:30:1:10 | 99.5 | 5.0 | 93.8 | 0.9 | 0.3 |
| 100:50:20:10 | 90.0 | 31.0 | 68.4 | 0.5 | 0.1 |
| 100:50:10:1 | 92.1 | 28.4 | 70.6 | 0.9 | 0.1 |

EXAMPLE 12

A reactant solution consisting of phenol, methanol, and water at a molar ratio of 1:5:1 was supplied at a rate of 1.6 cc/cat.cc.hr. in LHSV and subjected to reaction at a temperature of 350° C. in the presence of a varying iron oxide.indium oxide.chromium oxide.silicon oxide catalyst, iron oxide.indium oxide.chromium oxide catalyst or iron oxide.indium oxide.silicon oxide catalyst of a different composition prepared by following the procedure of Example 2. The results of reaction obtained at 8 hours' reaction time are shown in Table 9.

Comparative Experiment 3

The same reaction as in Example 12 was performed under the same reaction conditions in the presence of a varying iron oxide.chromium oxide.catalyst, iron oxide.silicon oxide catalyst, or iron oxide.indium oxide catalyst prepared by following the procedure of Example 2. The results of reaction obtained at 8 hours' reaction time are shown in Table 9.

TABLE 9

| No. | Catalyst composition (by atomic ratio) | Conversion of phenol (%) | Selectivity (%) | | | | Utilization ratio of methanol (%) |
|---|---|---|---|---|---|---|---|
| | | | o-cresol | 2,6-xylenol | 2,4,6-trimethyl phenol | Others | |
| Example 12 | Fe$_2$O$_3$.In$_2$O$_3$.Cr$_2$O$_3$.SiO$_2$ (Fe:In:Cr:Si = 100:7.5:1:1) | 99.97 | 0.68 | 98.7 | 0.54 | 0.08 | 57.9 |
| | Fe$_2$O$_3$.In$_2$O$_3$.Cr$_2$O$_3$.SiO$_2$ (Fe:In:Cr:Si = 100:2:1:1) | 92.5 | 15.9 | 83.4 | 0.50 | 0.3 | 56.9 |
| | Fe$_2$O$_3$.In$_2$O$_3$.Cr$_2$O$_3$ (Fe:In:Cr = 100:7.5:1) | 99.7 | 2.58 | 96.9 | 0.37 | 0.15 | 57.6 |
| | Fe$_2$O$_3$.In$_2$O$_3$.SiO$_2$ (Fe:In:Si = 100:7.5:1) | 99.1 | 6.16 | 95.3 | 0.30 | 0.54 | 55.8 |
| Comparative Experiment 3 | Fe$_2$O$_3$.In$_2$O$_3$ (Fe:In = 100:50) | 56.6 | 79.2 | 19.7 | 1.0 | 0.1 | 48.5 |
| | Fe$_2$O$_3$.SiO$_2$ (Fe:Si = 100:2) | 68.5 | 32.2 | 66.1 | 1.16 | 0.63 | 50.4 |
| | Fe$_2$O$_3$.Cr$_2$O$_3$ (Fe:Cr = 100:5) | 67.0 | 55.0 | 43.5 | 0.37 | 0.69 | 52.0 |
| | Fe$_2$O$_3$.Cr$_2$O$_3$.SiO$_2$ (Fe:Cr:Si = 100:1:1) | 75.0 | 30.4 | 68.1 | 1.02 | 0.48 | 53.6 |

EXAMPLE 13

The same reaction as in Example 11 was performed under the same reaction conditions in the presence of a varying catalyst prepared by the procedure of Example 1 using a varying alkali metal compounds. The results of reaction obtained at 24 hours' reaction time are summarized in Table 10.

TABLE 10

| | No. Example 13 | | | | |
|---|---|---|---|---|---|
| Catalyst composition (by atomic ratio) | Conversion of phenol (%) | Selectivity (%) | | | |
| | | o-cresol | 2,6-xylenol | 2,4,6-trimethyl phenol | Others |
| Fe$_2$O$_3$.In$_2$O$_3$.Cr$_2$O$_3$.KOH (Fe:In:Cr:K = 100:5:1:0.05) | 97.1 | 6.9 | 92.2 | 0.7 | 0.2 |
| Fe$_2$O$_3$.In$_2$O$_3$.SiO$_2$.KNO$_3$ (Fe:In:Si:K = 100:3.5:0.5:0.1) | 96.2 | 8.9 | 90.3 | 0.6 | 0.2 |
| Fe$_2$O$_3$.In$_2$O$_3$.Cr$_2$O$_3$.SiO$_2$.CsOH (Fe:In:Cr:Si:Cs = 100:10:1:5:0.01) | 99.9 | 4.8 | 94.4 | 0.6 | 0.2 |
| Fe$_2$O$_3$.In$_2$O$_3$.Cr$_2$O$_3$.SiO$_2$Li$_2$CO$_3$ (Fe:In:Cr:Si:Li = 100:7.5:2:2:0.1) | 100 | 1.0 | 98.3 | 0.6 | 0.1 |
| Fe$_2$O$_3$.In$_2$O$_3$.Cr$_2$O$_3$.SiO$_2$.Rb$_2$CO$_3$ (Fe:In:Cr:Si:Rb = 100:5:1:1:0.3) | 96.8 | 10.1 | 89.1 | 0.6 | 0.2 |
| Fe$_2$O$_3$.In$_2$O$_3$.Cr$_2$O$_3$.SiO$_2$.Na$_2$CO$_3$ (Fe:In:Cr:Si:Na = 100:3.5:1:1:0.05) | 95.2 | 12.6 | 86.5 | 0.7 | 0.2 |
| Fe$_2$O$_3$.In$_2$O$_3$.Cr$_2$O$_3$.SiO$_2$.KOH.CsOH (Fe:In:Cr:Si:K:Cs = 100:20:5:1:0.1:0.05) | 96.9 | 7.3 | 91.9 | 0.6 | 0.2 |
| Fe$_2$O$_3$.In$_2$O$_3$.Cr$_2$O$_3$.SiO$_2$.K$_2$CO$_3$ (Fe:In:Cr:K = 100:5:1:0.5) | 90.4 | 20.8 | 79.3 | 0.7 | 0.2 |

EXAMPLE 14

The reaction for producing an orthomethylated phenol compounds was carried out under a varying set of reaction conditions in the presence of the catalyst of Example 1 or the catalyst of Example 2. The results of reaction obtained at 8 hours' reaction time are shown in Table 11.

TABLE 11

| | No. Example 14 | | | | | |
|---|---|---|---|---|---|---|
| | Reaction conditions | | | | Selectivity (%) | |
| Catalyst composition (by atomic ratio) | Temperature (°C.) | LHSV (cc/cat. cc · hr) | Molar ratio* | Conversion of phenol (%) | o-cresol | 2,6-xylenol |
| $Fe_2O_3.In_2O_3.Cr_2O_3$ | 325 | 0.5 | 1/4/5 | 97.6 | 4.3 | 94.9 |
| $SiO_2.K_2CO_3$ | 380 | 5.0 | 1/7/1 | 99.3 | 2.1 | 97.2 |
| (Fe:In:Cr:Si:K = | 350 | 1.5 | 1/3/3 | 95.2 | 14.2 | 84.7 |
| 100:7.5:1:1 | 355 | 0.8 | 1/8/0 | 98.9 | 3.0 | 96.1 |
| :0.12) | | | | | | |
| $Fe_2O_3.In_2O_3.Cr_2O_3$ | 330 | 0.45 | 1/2.5/1 | 96.3 | 12.8 | 86.3 |
| $.SiO_2$ | 320 | 0.2 | 1/7/1 | 98.9 | 5.0 | 94.2 |
| (Fe:In:Cr:Si = | 370 | 3.0 | 1/8/2 | 97.2 | 5.9 | 93.3 |
| 100:7.5:1:1) | 360 | 2.5 | 1/6/5 | 96.9 | 8.1 | 91.1 |
| | 340 | 1.0 | 1/10/0 | 99.0 | 4.2 | 95.0 |

*phenol/methanol/water

EXAMPLE 15

Meta-cresol and methanol were reacted in the presence of the catalyst of Example 1.

A reactant solution consisting of meta-cresol, methanol, and water at a molar ratio of 1:5:1 was supplied at a rate of 0.7 cc/cat.cc.hr in LHSV and subjected to reaction at 340° C. The results of reaction at 8 hours' reaction time were 100 percent of meta-cresol conversion and 97.7 percent of selectivity for 2,3,6-trimethyl phenol.

EXAMPLE 16

Under the same reaction conditions as in Example 14, meta-cresol and methanol were reacted in the presence of the catalyst of Example 2. The results of reaction obtained at 8 hours' reaction time were 100 percent of meta-cresol conversion and 97.2 percent of selectivity for 2,3,6-trimethyl phenol.

EXAMPLE 17

One hundred (100) gr. of ferric nitrate, $Fe(NO_3)_3.9H_2O$, 6.6 gr. of indium nitrate, $In(NO_3)_3.3H_2O$, and 1.0 gr. of chromium nitrate $Cr(NO_3)_3.9H_2O$ were separately dissolved in water, neutralized with 10% ammonia water to pH 7.0, washed thoroughly with water, and filtered respectively. The gels thus obtained were mixed. The mixture was kneaded with an aqueous silica sol solution ($SiO_2$ content 1 weight percent) for five hours and then dried at 120° C. for 16 hours. The dried mixture was uniformly crushed to a particle size of 8 to 16 mesh and then sprayed with an aqueous 0.1 weight percent potassium carbonate solution. The particles were dried at 120° C. for 10 hours and subsequently calcined at 400° C. under a current of air for four hours to afford an iron oxide.indium oxide.chromium oxide.-silicon oxide.potassium carbonate catalyst.

The catalyst had a composition such that the atomic ratio of Fe:In:Cr:Si:K was 100:5:1:0.5:0.1.

In the presence of 2 ml of this catalyst, a reactant solution consisting of phenol, methanol and water in a molar ratio of 1:4:5 was supplied at a rate of 0.6 cc/cat.cc.hr. in LHSV and subjected to reaction at a reaction temperature of 345° C.

The results of reaction obtained at 100 hours' reaction time indicated that the conversion of phenol was 99.9 percent, the selectivity for ortho-cresol was 3.2 percent, that for 2,6-xylenol was 95.9 percent, that for 2,4-xylenol was 0.12 percent, that for 2,4,6-trimethyl phenol was 0.61 percent, the combined selectivity of anisoles such as anisole and trimethyl anisole was 0.17 percent, and that of m- and p-cresols was less than 0.01 percent respectively.

The utilization ratio of methanol was 56.4 percent. When the decomposed gas obtained at this point was analyzed by gas chromatography, it was found to be composed of 74.1 volume percent of $H_2$, 2.4 volume percent of $CH_4$, 0.5 volume percent of CO, and 23 volume percent of $CO_2$.

The results of reaction obtained at 500 hours' reaction time were practically the same.

What is claimed is:

1. A method for the manufacture of orthomethylated phenol compounds which comprises reacting phenol compounds having at least one hydrogen atom at the ortho position with methanol at a temperature of 250° C. to 500° C. and a space velocity of 0.05 to 10 in LHSV in the presence of a catalyst comprising:
   A. iron oxide,
   B. indium oxide, and
   C. at least one member selected from the group consisting of chromium oxide and silicon oxide.

2. The method according to claim 1, wherein the catalyst comprises said components A, B, and C plus
   D: at least one alkali metal compound.

3. The method according to claim 1, wherein the component C of the catalyst is chromium oxide and the atomic ratio of Fe:In:Cr is in the range of 100:0.5~50:0.05~20.

4. The method according to claim 1, wherein the component C of the catalyst is silicon oxide and the atomic ratio of Fe:In:Si is in the range of 100:0.5~50:0.05~10.

5. The method according to claim 1, wherein the component C of the catalyst is a combination of chromium oxide and silicon oxide and the atomic ratio Fe:In:Cr:Si is in the range of 100:0.5~50:0.05~20:0.05~10.

6. The method according to claim 2, wherein the component C of the catalyst is chromium oxide and the atomic ratio of Fe:In:Cr:alkali metal is in the range of 100:0.5~50:0.05~20:0.01~0.5.

7. The method according to claim 2, wherein the component C of the catalyst is silicon oxide and the atomic ratio of Fe:In:Si:alkali metal is 100:0.5~50:0.05~10:0.01~0.5.

8. The method according to claim 2, wherein the component C of the catalyst is a combination of chromium oxide and silicon oxide and the atomic ratio of Fe:In:Cr:Si:alkali metal is in the range of 100:0.5~50:0.05~20:0.05~10:0.01~0.5.

9. The method according to claim 1, wherein the molar ratio of methanol to the phenol compound is in the range of 1:1 to 10:1.

10. The method according to claim 2, wherein the molar ratio of methanol to the phenol compound is in the range of 1:1 to 10:1.

11. The method according to any of claims 3-8, wherein the molar ratio of methanol to the phenol compound is in the range of 1:1 to 10:1.

12. The method according to claim 1, wherein the phenol compound and methanol are used as diluted with water.

13. The method according to claim 2, wherein the phenol compound and methanol are used as diluted with water.

14. The method according to any one of claims 3-8, wherein the phenol compound and methanol are used as diluted with water.

15. The method according to claim 12, wherein the molar ratio of the phenol compound to water is in the range of 1:0.1 to 1:10.

16. The method according to claim 13, wherein the molar ratio of the phenol compound to water is in the range of 1:0.1 to 1:10.

17. The method according to claim 1, wherein the reaction is carried out at temperature in the range of 250° C. to 500° C.

18. The method according to claim 2, wherein the reaction is carried out at a temperature in the range of 250° C. to 500° C.

19. The method according to any one of claims 1-10, 12, 13, 15 and 16, wherein the reaction is carried out at temperature in the range of 300°-400° C.

20. The method according to any one of claims 1-10, 12, 13 or 15-18, wherein the reaction is carried out at a space velocity in the range of 0.1-5 in LHSV.

* * * * *